United States Patent [19]

Heine et al.

[11] Patent Number: 4,768,878

[45] Date of Patent: Sep. 6, 1988

[54] TEST ARRANGEMENT FOR NON-CONTACTING IDENTIFICATION OF DEFECTS IN NON-STRUCTURED SURFACES

[75] Inventors: Wolfgang Heine, Munich; Walter Huber, Puchheim, both of Fed. Rep. of Germany

[73] Assignee: Siemens Aktiengesellschaft, Berlin and Munich, Fed. Rep. of Germany

[21] Appl. No.: 905,186

[22] Filed: Sep. 9, 1986

[30] Foreign Application Priority Data

Sep. 9, 1985 [DE] Fed. Rep. of Germany ....... 3532117

[51] Int. Cl.$^4$ .......................................... G01N 21/00
[52] U.S. Cl. .................................. 356/237; 356/446; 350/162.11
[58] Field of Search ............... 356/237, 338, 336, 225; 250/446, 563, 572, 337 R; 350/162.11, 276 R, 276 SL, 319

[56] References Cited

U.S. PATENT DOCUMENTS

| | | | |
|---|---|---|---|
| 2,422,273 | 6/1947 | Wannamaker, Jr. | 356/43 |
| 3,917,414 | 11/1975 | Geis et al. | 356/200 |
| 4,175,865 | 11/1979 | Horvath et al. | 356/338 |
| 4,378,159 | 3/1983 | Galbraith | 356/237 |
| 4,601,576 | 7/1986 | Galbraith | 356/237 |

FOREIGN PATENT DOCUMENTS

| | | |
|---|---|---|
| 0146005 | 6/1985 | European Pat. Off. . |
| 1473681 | 2/1965 | Fed. Rep. of Germany ...... 356/237 |
| 2477288 | 9/1981 | France . |
| 0208408 | 11/1984 | Japan ................................. 356/237 |

Primary Examiner—Eugene R. LaRoche
Assistant Examiner—Seung Ham
Attorney, Agent, or Firm—Hill, Van Santen, Steadman & Simpson

[57] ABSTRACT

For the identification of defects in a non-structured surface, the surface to be investigated scanned with a scanning light ray wherein the light scattered and defracted by a defect is collected on a light sensitive surface of an opto-electronic receiver. In order to also be able to detect defects in a submicrometer range, a diaphragm for reducing the scattered light components in the scanning light ray prior to reaching the surface being tested is provided in the path of the scanning ray and has at least two diaphragm edges which are successively arranged in the diaphragm so that they respectively block out or cover only the shadow region of the preceding diaphragm edge. The test installation is particularly useful in testing a mask which has not yet been structured.

19 Claims, 3 Drawing Sheets

FIG 3
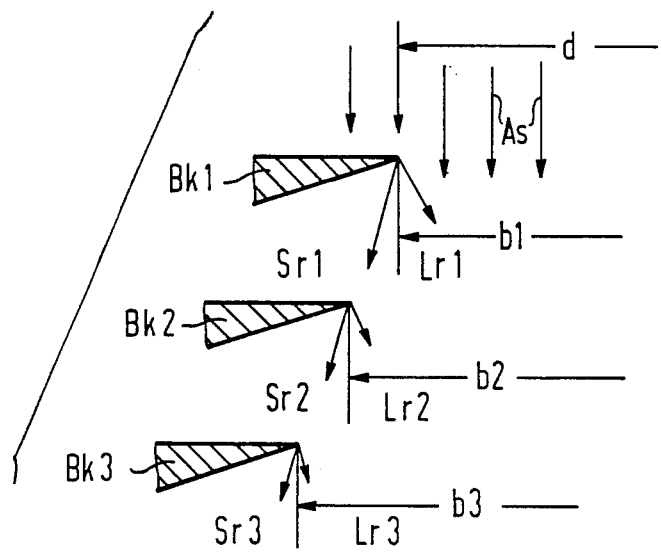
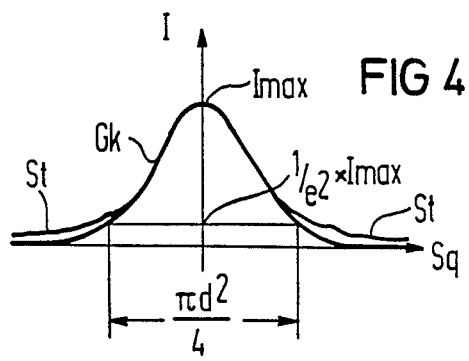
FIG 4
FIG 5
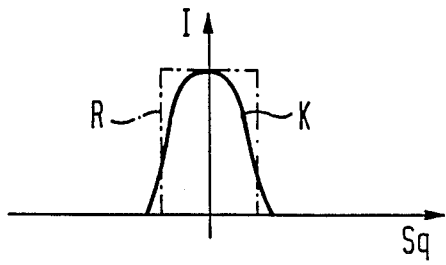

TEST ARRANGEMENT FOR NON-CONTACTING IDENTIFICATION OF DEFECTS IN NON-STRUCTURED SURFACES

BACKGROUND OF THE INVENTION

The present invention is directed to a test arrangement for non-contacting identification of defects in a non-structured surface. The test arrangement includes means for generating a scanning light ray, means for directing the light ray onto a non-structured surface, means for collecting light deflected at a defective location including an opto-electronic receiver for the detection of the collected light.

For locating defects in a non-structured surface, the surface of the unit under test, which is to be investigated, is scanned with a laser beam. The relative motion between the laser beam and the unit under test required for this purpose is thereby usually generated in the first direction by a scanning mirror arranged in the beam path and is generated in the second direction perpendicular to the first direction by displacing the unit under test. When the laser beam strikes a defective location, then the light is scattered or, respectively, defracted and can be detected as either reflected light or transmitted light via an opto-electronic receiver which supplies a signal corresponding to the detected defect. In order to supply the opto-electronic receiver with an optimumly great part of the light deflected at a defective location, this light is previously collected in a corresponding optical means. A hemisphere acting on the principle of Ulbricht's sphere is used, for example, as an optical collecting means and the hemisphere integrates the individual light rays coming from a defective location and thus, fully acquires them via the inside surface of the hemisphere. In addition to the spherical shape, however, many other shapes standard for optical collecting elements, such as elliptical hollow members, ellipsoids, parabolic hollow members of paraboloids and the like can be utilized.

In the known test arrangements, which are also frequently referred to as laser scanners, the laser beams employed as the scanning light ray has a relatively large halo, which in particular is attributed to light scatter of lenses, mirrored surfaces and the laser itself. This halo then causes unfavorable signal-to-noise ration so that smaller defects can no longer be reliably identified.

However, when checking as yet unstructured mask for semi-conductor technology, compact disk for either video or audio storage, and the magnetic storage disk, it is precisely a matter of acquiring even the smallest defect in the surface or in individual layers, and these defects may have a dimension in a sub-micrometer range.

SUMMARY OF THE INVENTION

The object of the present invention is to create a test installation for non-contact identification of defects in non-structured surfaces with which even the smallest defect having dimensions in sub-micrometer range can be reliably identified.

The objects are obtained in an improvement in a testing arrangement for non-contact identifying of defects in non-structured systems, said testing arrangement including a means for generating a scanning light ray, means for directing the scanning light ray on the surface being tested, means for collecting light deflected at a defective location of the surface including an opto-electronic receiver for the detection of the collected light. The improvements are that the means for directing the scanning light ray on the surface includes a positioning of a diaphragm for reducing the light scatter components in the beam path of the scanning light ray, said diaphragm having at least two diaphragm edges being successively arranged in the diaphragm so that every following diaphragm edge at least partially blocks the light defracted into a shadow space of the preceding diaphragm edge.

The invention is based on the perception that the light scatter components of the scanning light ray can be reduced to such a degree by means of a diaphragm inserted into the beam path that due to the corresponding improved signal-to-noise ratio, even the smallest defect in the sub-micrometer range can be reliably acquired. The prerequisite for such an effect of the diaphragm is that it thereby comprises at least two, preferably a plurality, of diaphragm edges arranged following one another so that every following diaphragm edge at least partially acquires or blocks the light defracted into the shadow space by the preceding diaphragm edge. Given such an arrangement, the defracted light is thus, reduced further with every diaphragm edge as seen in the direction of the scanning light rays so that the light beam profile of the scanning light beam is modified in the direction towards a rectangular shape.

In accordance with the preferred embodiment of the invention, the diaphragm edges are arranged following one another such that every following diaphragm edge cuts the first secondary maximum of the light defracted into the allocated shadow space by the preceding diaphragm edge. A particularly great part of the light scatter is rendered ineffective by means of such a cut-out of the secondary maximums.

The diaphragm edges are preferably fashioned as sharp knife edges whereby the reflecting surface of the diaphragm edges in the component of the light reflected at them are reduced. In addition, it is also advantageous when the region of the diaphragm lying between the diaphragm edges comprise a light absorbing surface so that the light defracted into the shadow space is absorbed and can thus, be rendered ineffective.

Given test installations, wherein the deflection means is arranged in the beam path of the scanning light ray, the diaphragm is expediently arranged following the deflection means as seen in the direction of the scanning light ray. The diaphragm can then also block the light scatter generated by the deflecting means, for example, a scanning mirror, and can reduce it or, respectively, neutralize it.

Given an employment of deflection means for the scanning light ray, the diaphragm edges are then preferably aligned parallel to the deflection plane of the scanning light ray so that the passage of the light component desired for the scanning is not impeded. The inverse product of the scanning light ray can then have additional diaphragm edges of the diaphragm allocated to them so that the light scatter component can also be reduced in the region of these reversal points in the path of the light.

In accordance with the particular preferred development of the invention, the diaphragm edges are formed by a saw-toothed profile on the side wall of the diaphragm which side walls lie opposite to one another. As a result thereof, the manufacture of the diaphragm is considerably simplified and a fixed relative position of the diaphragm edge on a side wall is guaranteed. Moreover, a plurality of diaphragm edges can be accommodated in a tiny space by means of the saw-toothed profiles. These advantages also occur when the additional diaphragm edges are formed by a saw-toothed profile on the inside of the end walls of the diaphragm which lie opposite one another and are inclined oppositely relative to one another. The diaphragm edges are then preferably arranged offset relative to the additional diaphragm edges so that the diaphragm edges in the additional diaphragm edges can engage into one another in the corner region of the diaphragm without disturbing one another. When the two side and the two end walls of the diaphragm are then displaceable and adjustably connected to one another, then the effect of the diaphragm can be optimized in a simple way by means of an appropriate adjustment.

In view of the optimumly effective reduction of the scatter light component, it is also particularly advantageous when the width of the diaphragm gap formed by the first diaphragm edge at least approximately corresponds to the diameter of the scanning light ray.

The rays defracted into the light space by the diaphragm edges can pass through the diaphragm when they are steeper than the diagonal between the first and the last diaphragm edges. The diaphragm angle should therefore be kept as small as possible. This is achieved by means of an appropriate dimensioning with the spacing between the first diaphragm edge and the last diaphragm edge corresponding to at least ten times the value of the diameter of the standing light ray. Preferably, this distance or spacing is at least in a range of 100 through 200 times the value of the diameter of the scanning light ray.

BRIEF DESCRIPTION OF THE DRAWINGS

FIG. 3 is an enlarged partial cross sectional view of the diaphragm edges of the diaphragm of FIG. 2;

FIG. 4 is a graph illustrating the light intensity relative to the diameter for the beam profile of the scanning light beam; and FIG. 5 is a beam profile of the intensity to the beam diameter of the beam after it has passed through the diaphragm of the present invention.

DESCRIPTION OF THE PREFERRED EMBODIMENTS

Figure 1:
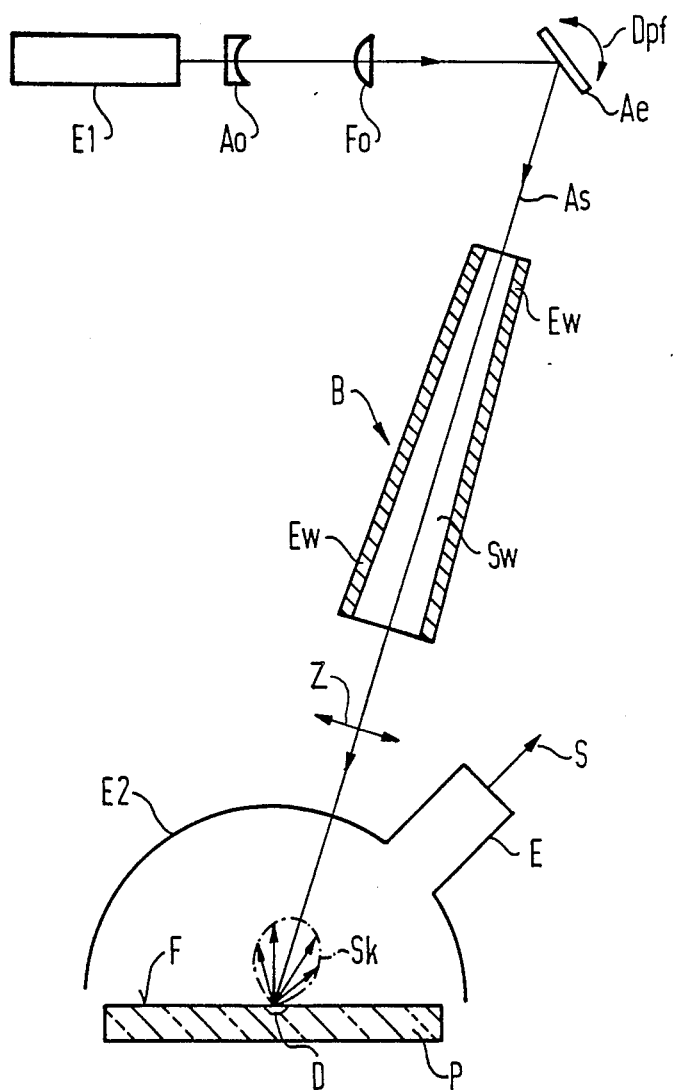
FIG. 1 is a schematic illustration of a test installation for non-contact identification of defects in a non-structured surface in accordance with the present invention.

The principles of the present invention are particularly useful when incorporated in a test installation which is schematically illustrated in the FIGS. The test installation is for non-contacted identification of defects D in a non-structured surface F of a unit P. The arrangement or installation includes means E1 for generating a scanning ray As. As the light leaves the light generating means E1, it passes through an expanding optics Ao then to a focussing optics Fo to a deflecting means Ae which deflects it through a diaphragm B for reducing the light scatter components of the beam.

After passing through the diaphragm B, the scanning light ray As is periodically moved back and forth by the deflecting means Ae in a direction indicated by the double arrow Z, which is in the plane of the drawings, due to the rotation of the deflecting means Ae as indicated by the double arrow Dpf. The light will extend through a slit in a means E2 to strike the surface F, which is to be investigated, of the unit P under test. In addition to the already mentioned excursion of the scanning light rays, the unit P is dislocated in a direction perpendicular to the plane of the drawings so that the surface F is scanned by the scanning light rays. In order to magnify the region of the surface, which is to scanned and which surface F can also be an intermediate layer, the unit P can also be moved with a meandering-shaped path when requested.

When the scanning light rays As impinge faultless regions of the surface F then the light is in the reflected direction again leaves the means E2 through the slit through which it is entered. When by contrast the scanning light rays impinge or strike a defect D, which can be a pore on the surface F, an inclusion of a foreign body, a contamination of the surface or the like, then the light is scattered and defracted and the corresponding scattered lobe is reference Sk. The light scattered and defracted at the defect location is then at least partially collected by the means E2 and directed or collected into light sensitive surfaces of an electro-optical receiver E whose output signal S indicates the detected defect D.

In particular, the means E1 is preferably a laser, for example, a HeCd laser, whose emmission is expanded to a diameter of 4 mm and the expanding optics Ao from an initial diameter of 1 mm. The expanding laser beam is then focussed onto the surface F by the focussing optics Fo so that the diameter of the beam at the point of incidence amounts to 50 μm.

The diaphragm B comprises two side walls Sw and two end walls Ew. The position inclination of the two end walls is matched to the maximum excursion of the scanning light ray As. The two side walls Sw are arranged shortly before or, respectively, following the deflection plane of the scanning rays As and lie in the plane of the drawing. Further details regarding the structure and the functioning of the diaphragm B are set forth later with reference to FIGS. 2-5.

The means E2 for collecting light deflected at the deflecting location is a hemisphere opened towards the bottom which is arranged above the surface F of the unit P under test. As in the case of the spherical photometer of the Ulbricht, the hemisphere is painted matte white on the inside so that the light scattered and defracted at the deflected defect D is repeatedly and diffusedly reflected so that every surface element on the inside surface of the hemisphere is illuminated to approximately the same degree. In this way, the light rays coming from the defect D are acquired and one partially supplied to the light sensitive surface of the electro-electronic receiver E, which may be, for example, a photo-multiplier and this receiver lies in the region of the inside surface of the hemisphere. Other forms of the means or receiver E, which likewise meet the desired collection functions, are likewise possible. Departing from the investigation of the surface F and incident light as shown, the investigation can also be undertaken in transmitted light wherein the means E2 is then correspondingly arranged on the underside of the unit P.

Figure 2:
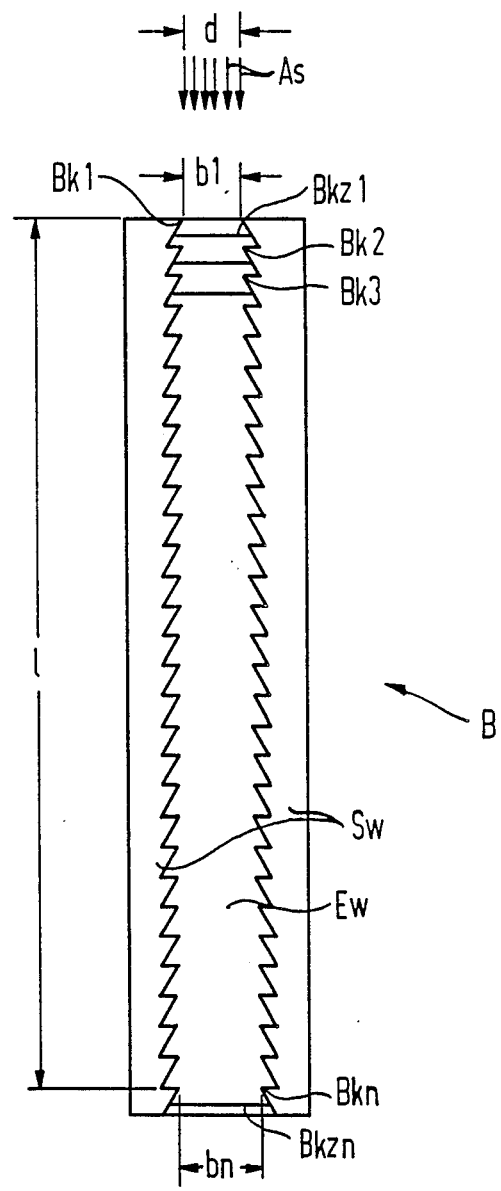
FIG. 2 is a side view of the diaphragm employed in the test arrangement of FIG. 1 with a portion removed for purposes of illustration.

The diaphragm B is illustrated in FIG. 2 with a front end wall Ew removed. The insides of the side walls Sw are provided with saw-toothed-shaped profiles by means of which the diaphragm edges Bk1, Bk2, . . . , Bkn are provided and lie opposite each other at the same height. As illustrated, n equals 30. The diaphragm edges Bk1 through Bkn proceed towards the back perpendicular to the plane of the drawings and form diaphragm gaps whose width b1—bn increase in the direction of the scanning light ray As passing through the diaphragm B. Each of the end walls Ew has a saw-toothed-shaped profile of diaphragm edges Bkz1 . . . Bkzn and the inside wall surfaces of the two end walls Ew are inclined at an angle relative to one another. These additional diaphragm edges Bkz1 through Bkzn are allocated to the reversal point of the scanning light rays As and are offset relative to the diaphragm edges Bk1 through Bkn so that no mutual impediment can occur in the corner regions of the diaphragm B when all the walls are assembled together. As illustrated, the walls can be assembled together and displaced in an adjustable fashion with the two side walls Sw being offset relative to the two end walls Ew. The two side walls Sw and the two end walls Ew are composed of aluminum and the profiles on the inside surfaces are respectively anodically oxidized to a matte black. The width b1 of the diaphragm gap formed by the first diaphragm edges Bk1 preferably corresponds to the diameter d of the scanning light ray As indicated by arrows and amounts to 1 mm in the illustrated examplary embodiment. The width bn of the diaphragm gap for by the last diaphragm edge Bkn by contrast amounts to 1.5 mm. The spacing or distance 1 between the first diaphragm edges Bk1 and the last diaphragm edges Bkn is preferably of a value of at least 10 times the diameter d of the scanning light ray As. Preferably, the spacing 1 falls in a range of at least 100–200 times the value of the diameter d for the scanning light rays As.

The principles of the functioning of the diaphragm B is best illustrated in FIG. 3; however, only three diaphragm edges Bk1, Bk2 and Bk3 are illustrated. The first diaphragm edge Bk1 forms a diaphragm gap having a width of b1 whose light space is referenced Lr1 and whose shadow space is reference Sr1. The second diaphragm edge Bk2 forms a diaphragm gap having a width b2 whose light space is referenced Lr2 and whose shadow space is Sr2. The third diaphragm edge Bk2 forms a diaphragm gap having a width b3 whose light space is referenced Lr3 and whose shadow space is Sr3.

The width b1 of the diaphragm gap formed by the first diaphragm edge Bk1 is dimensioned so that it is at least approximately identical to the diameter d of the scanning light rays As. The first diaphragm edge Bk1 then defracts the light both into a shadow space Sr1 as well as into a light space Lr1. The second diaphragm edge Bk2 is now arranged so that in the shadow space Sr1 it will cut or block the first secondary maximum of the light which the first diaphragm edge Bk1 deflects into the allocated shadow space Sr1. The second diaphragm edge Bk2 then again defracts both into the allocated shadow space Sr2 as well as into the allocated light space Lr2. In accordance with the function principles set forth above, the third diaphragm edge Bk3 is then arranged so that it will cut or block the first secondary maximum of the light which was defracted by the second diaphragm edge Bk2 into the allocated shadow space Sr2. It may be seen that the defracted light is continuously reduced in the direction of the scanning light rays As and thus, the halo of the scanning light rays As is reduced further and further.

In FIG. 4, the intensity I of the scanning light rays As is illustrated before entry into the diaphragm B. This representation is based on intensity versus beam cross section Sq. The resulting bell curve of Gaussian distribution curve is referenced Gk where as the undesired light scatter components of the scanning light ray As are indicated by the curve branches St. Given the intensity $I=1/e^2$. Imax, the beam cross section $Sq = \pi d^2/4$ wherein d is the forementioned diameter of the scanning light ray.

The intensity of the scanning light ray As after exit from the diaphragm B is plotted against the beam cross section Sq and produces a curve K of FIG. 5. It may be seen that the effect of the diaphragm B and the shadowing of the light scattering laterally cuts or clips the typical bell-shaped curve Gk of FIG. 4 and the resulting curve K approaches a rectangular shape R indicated in dot-dash lines. The halos of the scanning light ray As is at least largely eliminated by the action of the diaphragm B. As a result thereof a signal-to-noise ratio of the test installation shown in FIG. 1 is improved so that even extremely small defects having a dimension in the sub-micrometer region can be reliably detected.

Although various minor modifications may be suggested by those versed in the art, it should be understood that we wish to employ within the scope of the patent granted hereon, all such modifications as reasonably and properly come within the scope of our contribution to the art.

We claim:

1. In a test arrangement for non-contact identification of defects in a non-structured surface, said arrangement including means for generating a scanning light ray, means for directing the light ray onto the non-structured surface, means for collecting the light deflected at a defective location of said surface including an opto-electronic receiver for the detection of collected light, the improvements comprising a diaphragm for reducing the light scatter components being arranged in the beam path of the scanning light ray, said diaphragm having at least two diaphragm edges being successively arranged in said diaphragm in the direction of light passing therethrough so that every following diaphragm edge at least partially blocks out light defracted into a shadow region by a preceding diaphragm edge.

2. In a test arrangement according to claim 1, wherein the diaphragm edges are arranged following one another so that the following edges cut the first secondary maximum of the light defracted into the allocated shadow space by the preceding diaphragm edge.

3. In a test arrangement according to claim 1, wherein the diaphragm comprises a plurality of diaphragm edges arranged following one another.

4. In a test arrangement according to claim 1, wherein the diaphragm edges are fashioned as sharp knife edges.

5. In a test arrangement according to claim 1, wherein the region of the diaphragm lying between the diaphragm edges comprises a light absorbing surface.

6. In a test arrangement according to claim 1, wherein the means for directing the light beam include a deflecting means arranged in the beam path for deflecting the light in a deflection plane and wherein the diaphragm is arranged following said deflecting means as seen in the direction of the scanning light rays.

7. In a test arrangement according to claim 6, wherein the diaphragm edges are respectively aligned parallel to the deflection plane of the scanning light rays.

8. In a test arrangement according to claim 7, wherein the diaphragm has a second set of diaphragm edges which are positioned for coaction with the scanning light ray as it approaches the reversal points of its deflection in the scanning plane.

9. In a test arrangement according to claim 7, wherein the diaphragm edges are formed by a saw-toothed profile on the inside side wall of a diaphragm which lie opposite one another.

10. In a test arrangement according to claim 9, wherein the diaphragm has additional diaphragm edges being formed as saw-toothed profiles on inside surfaces of end walls of the diaphragm lying opposite of one another and being inclined in an opposite direction.

11. In a test arrangement according to claim 10, wherein the diaphragm edges on the side walls are offset relative to the additional diaphragm edges on the end walls.

12. In a test arrangement according to claim 11, wherein the two sides walls and the two end walls of the diaphragm are connected to one another in a displaceable and adjustable fashion.

13. In a test arrangement according to claim 10, wherein the width of the diaphragm gap formed between the first diaphragm edges is at least approximately corresponds to the diameter of the scanning light ray.

14. In a test arrangement according to claim 7, wherein the width of the diaphragm gap formed by the first diaphragm edges at least approximately corresponds to the diameter of the scanning light ray.

15. In a test arrangement according to claim 1, wherein a spacing between the first diaphragm edge and the last diaphragm edge corresponds to at least 10 times the value of the diameter of the scanning light ray.

16. In a test arrangement according to claim 14, wherein the spacing between the first diaphragm edge and the last diaphragm edge is in a range of 100 to 200 times the value of the diameter of the scanning light ray.

17. A test arrangement for non-contact identification of defects in a non-structured surface, said arrangement comprising means for generating a scanning light ray, means for directing the light ray onto the non-structured surface, said means for directing including lens for focusing the rays into a beam and deflecting means arranged in a path of the beam for deflecting the light ray in a deflection plane in a deflection path, means for collecting the light deflected at a defective location of said surface including an opto-electronic receiver for the detection of collected light, and a diaphragm for reducing the light scatter components being arranged in the beam path of the scanning light ray between the deflecting means and means for collecting, said diaphragm having a box-like housing with two end walls and two side walls forming a rectangular opening having a width approximately equal to the cross section of the beam and a length equal to the deflection path, said diaphragm having at least two diaphragm edges being successively arranged on each side wall in the direction of light passing therethrough, and at least two additional diaphragm edges being successively arranged on each end wall in the direction of light passing therethrough, each of the diaphragm edges being a sharp edge with regions between adjacent edges being light absorbing surfaces, the spacing between a pair opposite edges increase as the distance of each pair from the deflecting means increases so that every following diaphragm edge at least partially blocks out light defracted into a shadow region by a preceding diaphragm edge.

18. A test arrangement according to claim 17, wherein each diaphragm edge has a saw tooth configuration.

19. A test arrangement according to claim 18, wherein the diaphragm edges on the side walls are offset relative to the additional diaphragm edges on the end walls.

* * * * *